(12) United States Patent
Proffitt et al.

(10) Patent No.: US 6,770,290 B1
(45) Date of Patent: *Aug. 3, 2004

(54) AMPHOTERICIN B LIPOSOME PREPARATION

(75) Inventors: Richard T. Proffitt, Arcadia, CA (US); Jill Adler-Moore, Altadena, CA (US); Su-Ming Chiang, Canoga Park, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/600,154

(22) Filed: Oct. 19, 1990

Related U.S. Application Data

(63) Continuation of application No. 07/119,518, filed on Nov. 12, 1987, now abandoned.
(51) Int. Cl.$^7$ .......................... A61K 9/127; A61K 31/70; C07M 1/00
(52) U.S. Cl. .......................... 424/450; 536/6.5; 514/31
(58) Field of Search .......................... 424/150; 536/6.5; 514/31; 423/450

(56) References Cited

U.S. PATENT DOCUMENTS

| | | | |
|---|---|---|---|
| 4,394,149 A | | 7/1983 | Szoka .......................... 71/28 |
| 4,497,791 A | | 2/1985 | Gamble et al. .............. 424/1.1 |
| 4,622,219 A | | 11/1986 | Haynes .......................... 424/38 |
| 4,663,167 A | * | 5/1987 | Lopez-Berestein et al. ... 514/37 |
| 4,744,989 A | * | 5/1988 | Payne et al. .................. 514/3 |
| 4,766,046 A | | 8/1988 | Abra et al. ................. 424/450 |

FOREIGN PATENT DOCUMENTS

| | | |
|---|---|---|
| EP | 0028917 | 5/1981 |
| EP | 0119020 | 9/1984 |
| EP | 1794444 | 4/1986 |
| EP | 0272091 | 6/1988 |
| JP | 33774 E/17 | 3/1982 |
| WO | 8203769 | 11/1982 |
| WO | 8505030 | 11/1985 |
| WO | 8601103 | 2/1986 |
| WO | 8806443 | 9/1988 |

OTHER PUBLICATIONS

New, Antileishmanial Activity of Amphotericin and Other Antifungal Agents Entrapped in Liposomes, J. Antimicrobial Chemotherapy (1981) 8, 371–381.

Lopez–Berestein et al., Treatment of Hepatosplenic Candidiasis with Liposomal–Amphotericin B, J. Clin. Oncology (1987) 5, 310–317.

Medoff, G. Kabayashi, G, Strategies and Treatment of System Fungal Infections, N. Eng. J. Med., 302, pp. 145–155 (1980).

Cohen, J., Antifungal Chemotherapy, Lancet, II, pp. 532–537 (1982).

Graybill, J.R. Craven, P.C., Antifungal Agencies and System Mycosis: Activity and Theraputic Use, Drugs, 25, pp. 41–62 (1983).

Mehta, R., Amphotericin B is Toxic to Fungal Cells but not to Mammalian cells, Biochimica Et Biophysica Acta, 770, pp. 230–234 (1982).

Graybill, Jr. R. et al., Treatment of Murine Cryptococcoses Liposomal Associated Amphotericin B., J. Infect. Dis., 145, pp. 748–752 (1983).

Lopez–Berestein, G. et al., Treatment of Hepatosplenic Candidiasis with Liposomal Amphotericin B, J. Clinc. Onc., 5, pp. 310–317 (1987).

New, Antileishmanial Activity of Amphotericin and Other Antifungal Agents Entrapped in Liposomes, 1981, 371–381, Journal of Antimicrobial Chemotherapy.

Lopez–Berestein, G., Treatment and Prophylaxis in Disseminated Infection Due to Candida Albicans, with Liposome Encapsulated Amphotericin B. J. Infect. Dis., 147, pp. 939–945 (1983).

Gregoriadis, G. A. (Ed.), *Liposome Technology*, CRC Press: Boca Raton, Florida (1983).

* cited by examiner

*Primary Examiner*—Elli Peselev
(74) *Attorney, Agent, or Firm*—Mark L. Bosse

(57) ABSTRACT

A novel composition and method for solubilizing amphiphilic drugs in a small amount of organic solvent for use in improved liposomes is disclosed. A phosphatidylglycerol is acidified in a small amount of organic solvent. The amphiphilic drug, such as Amphotericin B, suspended in organic solvent is then added to the acidified phosphatidylycerol and a soluble complex is formed between the phosphatidylglycerol and the amphiphilic drug. When the liposome composition incorporating the soluble complex is hydrated, the final pH of the hydrating aqueous buffer is carefully controlled. The Amphotericin B liposomes formed have markedly reduced toxicity.

9 Claims, No Drawings

AMPHOTERICIN B LIPOSOME PREPARATION

This application is a continuation of copending U.S. patent application Ser. No. 07/119,518 filed Nov. 12, 1987, now abandoned.

FIELD OF THE INVENTION

This invention relates to a novel procedure for solubilizing amphiphilic drugs. In another aspect, this invention relates to improved methods of Amphotericin B liposome preparation. In another aspect this invention relates to improved methods of producing liposomes by a commercially feasible process. This invention also relates to liposomal Amphotericin B having reduced toxicity and to a new method of treatment with liposomal Amphotericin B.

BACKGROUND OF THE INVENTION

Systemic fungal infections are a major cause of mortality in cancer patients and other immunocompromised individuals. Unfortunately, fungal infections very often defy treatment because the few drugs that destroy fungi are extremely toxic to the host. Because of the drugs' toxicity, the lowest possible effective doses should be given. Unfortunately, because the drugs are diluted in the blood, and because large amounts of the drugs are degraded, or excreted or taken up by uninfected tissue, large doses actually are and must be given if the treatment is to be effective.

The preferred treatment for systemic fungal infections is primarily limited to two groups of drugs: the polyene antibiotics such as Amphotericin B and nystatin, and the imidazoles, such as ketaconazole and miconazole. The polyene antifungal antibiotics readily bind to sterol components of host cells causing disruption of the membrane, cell permeability and lysis. Amphotericin B has thus been associated with acute hemolytic crisis. Further, because it is particularly toxic to kidney tissue, it has been associated with irreversible renal damage and even kidney failure, at therapeutic dosage levels. Medoff, G., Kabayashi, G. (1980) Strategies in treatment of systemic fungal infections. *New England Journal of Medicine* 302: 145–55; Cohen, J. (1982) Antifungal chemotherapy. Lancet ii: 532–37; Graybill, J. R., Craven, P. C. (1983) Antifungal agents used in systemic mycosis: activity and therapeutic use. *Drugs* 25: 41–62.

It is a major goal of medical research to overcome the problems presented by the need for compromise between dosages high enough to control infection on the one hand, and unacceptable damage to healthy tissues on the other. Recently it has been discovered that needed doses of medicine can be delivered to diseased tissue while bypassing healthy tissue using certain liposomal formulations. Additionally, it has been recognized that medication can be incorporated into liposomes, microscopic delivery vesicles made, in part, of phospholipids. See U.S. Pat. No. 4,663,167—Composition and Method for Treatment of Disseminated Fungal Infections in Mammals, incorporated here by reference, and Vestar application Ser. No. 899,064 entitled "Improved Treatment of Systemic Fungal Infections with Phospholipid Particles Encapsulating Polyene Antifungal Antibiotics" (now U.S. Pat. No. 5,043,107), also incorporated by reference, . . . "which discloses liposomal delivery vesicles made, in part, from phospholipids.

Phospholipids form closed, fluid filled spheres when mixed with water. Phospholipid molecules are polar, having a hydrophilic ionizable head, and a hydrophobic tail consisting of long fatty acid chains. Thus, when sufficient phospholipid molecules are present with water, the tails spontaneously herd together to exclude the water while the hydrophilic phosphate heads form bonds with the water. The result is a bilayer in which the fatty acid tails point into the newly formed membrane's interior and the polar heads point toward the aqueous medium. The polar heads at one surface of the membrane point toward the liposome's aqueous interior and those at the other surface point toward the aqueous exterior environment. It is this chemical tendency to form liquid filled spheres that allows the liposome to be loaded with medication. As the liposomes form, water soluble molecules will be incorporated into the aqueous interior, and lipophilic molecules will tend to be incorporated into the lipid bilayer. Liposomes may be either multilamellar, like an onion with liquid separating many lipid bilayers, or unilamellar, with a single bilayer surrounding an entirely liquid center.

In studies of mice, Amphotericin B incorporated into liposomes has been shown to treat systemic fungal infections more effectively than when given as the free drug. Liposomes are not themselves toxic, and they protect their loads from being degraded or diluted. Thus, liposomes are thought to deliver concentrated doses of antifungal antibiotic at the diseased tissue without the toxicity that would otherwise be associated with freely circulating drug. Therefore, liposomal Amphotericin B drug doses can exceed the maximum tolerated dose of free Amphotericin B. Mehta, R. (1982), Liposomal aphotericin B is toxic to fungal cells but not to mammalian cells. *Biochimica et Biophysica Acta* 770: 230–34. Liposomal encapsulated Amphotericin B has also been shown to be an effective treatment for murine systemic fungal infections, including Candidiasis, Cryptococcosis, and Histoplasmosis. Graybill, J. R. et al (1983) Treatment of murine cryptococcosis with liposomal associated Amphotericin B. *Journal of Infectious Diseases* 145: 748–52; Taylor, R. L. et al (1982) Amphotericin B in liposomes: A novel therapy for histoplasmosis. *American Review of Respiratory Diseases* 125: 610–611.

Liposomal Amphotericin B has also shown effectiveness in human patients, life saving when other treatments have failed, including freely circulating Amphotericin B. Systemic fungal infections are seen most commonly in people whose immune systems are compromised by disease or immunosuppressive drug therapy. As previously mentioned, these infections are a common cause of death to victims of acquired immune deficiency syndrome and to cancer patients undergoing chemotherapy. The causative agents of these fungal infections are often endogenous fungi that would be rendered harmless but for the patient's impaired resistance. Lopez-Berestein, G. et al (1987) Treatment of hepatosplenic Candidiasis with liposomal Amphotericin B. *Journal of Clinical Oncology* 5:310–17.

Unfortunately, because of the chemical properties of the polyene antifungal antibiotics, it has heretofore not been possible to produce liposomal Amphotericin B in commercial quantities. These antifungal agents are called polyenes because they contain three to seven conjugated double bonds in the aliphatic chain making up a large lactone ring. The double bonds are incorporated into one side of the ring of 26 to 44 carbon atoms and along the opposite side of the ring 6 to 12 hydroxyl groups are present. Additionally, these molecules contain specific carboxylic acid groups and amine groups. Amphotericin B and nystatin, for example, possess both an aminosugar and a carboxylic acid group. The polyene regions of the molecules are of course hydrophobic and lipophilic while the polyol and ionizable regions are hydrophilic and lipophobic. As such, these molecules are called amphiphilic. Additionally, because of the carboxylic group and the amine group, Amphotericin B can act as a Lowry-Brønsted acid or proton donor, or as a Lowry-Brønsted base or proton acceptor. The combination of these functionalities makes polyenes very poorly soluble in water and most organic solvents. Bennett, J. E. (1974) Chemotherapy of systemic mycoses. *New England J. Medicine* 290: 320–23.

It has been the persistent problem of insolubility of the polyene antifungal antibiotics in general and of Amphotericin B in particular that has previously limited the prior art. Liposomal Amphotericin B formation was heretofore limited to generally two methods, described below, neither feasible for commercial scale production and neither showing long-term stability or as great a reduction in toxicity as the preparations herein described.

One prior method requires that the Amphotericin B be first dissolved in large volumes of volatile organic solvent such as methanol. To that solution would then be added the lipid mixture dissolved in a volatile organic solvent such as methanol and/or chloroform. The solvents would then have to be removed from the mixture to form a lipid-Amphotericin B film. Removal of solvents could be accomplished by a variety of methods but usually by evaporation to dryness in a round bottom flask under vacuum or nitrogen. Taylor, R. L. (1980) Amphotericin B in liposomes: A novel therapy for histoplasmosis. *Am. Review Respiratory Disease* 125: 610–11; Graybill, J. R. et al (1982) Treatment of murine crytococcosis diseases. *J. Infectious Diseases* 145: 748–52; Lopez-Berestein, G. (1983) Treatment and prophylaxis in disseminated infection due to Candida albicans in mice with liposome-encapsulated Amphotericin B. *J. Infectious Diseases* 147: 939–45; U.S. Pat. No. 4,663,167—Composition and method for treatment of disseminated fungal infections in mammals. The prior art methods thus required removal of large volumes of organic solvent, and preparation of a lipid-Amphotericin B film, an extra step eliminated by the present invention. Moreover, the prior art methods were thus practicable only in discrete batches and were not amenable to the continuous flow process of the current invention. These are two disadvantages which the industry has long attempted to overcome.

In another method of forming liposomal Amphotericin B, the lipid mixture is dissolved in chloroform or another solvent and deposited and dried on the sides of a round bottom flask or vesicle surface. A solution of Amphotericin B dissolved in a small amount of dimethyl sulfoxide would then be added to the previously deposited lipid film. The resulting preparation would thereafter have to be dialyzed against a buffered saline or other solution to remove the dimethyl sulfoxide and non-intercalated Amphotericin B. The procedure was extremely time consuming and expensive, and typically resulted in incorporation of only 70% of the initial Amphotericin B. Tremblay, C. et al (1984) Efficacy of liposome-intercalated Amphotericin B in treatment of systemic Candidiasis in mice. *Antimicrobial Agents and Chemotherapy* 26: 170–73.

Prior to the present invention, it was not possible to dissolve Amphotericin B in small quantities of volatile solvent, such that scaled-up production could be commercially feasible. The present invention also enables the dissolved Amphotericin B—phospholipid liposomal solution to be spray dried, thus making commercial quantities practical by elimination of the elaborate and time consuming steps detailed above.

Accordingly, one object of the present invention is to provide an improved process for the solubilization of amphophilic drugs.

Another object of the present invention is to provide an improved process for the encapsulation of polyene antifungal antibiotics into liposomes.

More specifically, an object of the present invention is to provide an improved process for the formation of liposomal Amphotericin B.

Yet another object of the present invention is to provide a commercially feasible process for the production of liposomal Amphotericin B.

Yet another object of the present invention is to provide a process for the formation of liposomal Amphotericin B with reduced toxicity.

A further object of the present invention is to provide new methods of treatment with Amphotericin B.

The manner in which these and other objects are realized by the present invention will be apparent from the summary and detailed description set forth below.

SUMMARY OF THE INVENTION

According to the present invention, the steps of either evaporation of the large volumes of volatile solvent into which the antibiotic is at least minimally soluble, or of removing a nonvolatile solvent in which the antibiotic and lipid has been dissolved, typically by dialysis, have been eliminated. Instead, the present invention provides a new and useful lipophilic charge complex of Amphotericin B which overcomes the previous problems of insolubility. Additionally, the present invention provides a new and useful process for the production of Amphotericin B liposomes suitable for scaling up production to commercial quantities. Additionally, the invention provides a method for production of Amphotericin B liposomes of increased stability and decreased toxicity.

In one preferred embodiment of this invention, the new soluble complex is formed between Amphotericin B and distearoyl-phosphatidylglycerol which has been protonated during dissolution in a solution of chloroform and methanol acidified to a pH of about 1.0 to 3.0. The Amphotericin B—phospholipid complex, while in solution in the small amount of acidified chloroform and methanol, can be mixed with phosphatidylcholine and cholesterol and reproducibly spray dried under controlled conditions to yield a lipid powder which is readily processed into liposomes, using an aqueous buffer solution having a pH such that the pH of the final solution is below about 5.5, preferably between about 4.5 and 5.5. Accordingly, the present invention allows commercial scaling up of new materials for liposomal production. Further, the liposomes formed with this invention can be lyophilized and stored for later rehydration and injection without significant change in size or toxicity. The advantages of the present invention, will become clear after considering the following detailed description.

DETAILED DESCRIPTION OF THE INVENTION

Distearoylphosphatidylglycerol, or other homologous phosphatidylglycerols, such as dilaurylphosphatidylglycerol, dimyristoylphosphatidylglycerol or others, is dissolved in an equal volume solution of chloroform and methanol and acidified before forming the described soluble complex with Amphotericin B. Thus, 2.5 N hydrochloric acid is added to the distearoylphosphatidylglycerol sodium salt solution in methanol:chloroform (1:1) to adjust the pH to between 1.0 and 3.0, as measured on prewetted pH paper, prior to mixing with Amphotericin B, and thereby acidifying the phospholipid. The Amphotericin B, or other polyene such as a tetraene, pentaene, or hexaene, is suspended in an equivolume solution of chloroform and methanol and then added to the acidic distearoylphosphatidylglycerol solution. Complex formation is facilitated by briefly warming the solution to about 65° Centigrade. At this stage, the concentration of Amphotericin B may be in excess of 45 mg/ml.

In the resulting solution additional lipids such as phosphatidylcholines may also be dissolved. Cholesterol or another sterol, such as ergosterol, stigmosterol, or androsterone, is included to improve the stability of the resulting liposomes, and thus maintain the liposome intact during circulation in the bloodstream. The solution is a translucent orange. Typically, the Amphotericin B concentration in the final solution is greater than 25 mg/ml, and the total dissolved solid material 15–20 percent by weight.

Among the additional phosphatidylcholines that may be dissolved in the Amphotericin B, acidic phosphatidylglycerol complex solution, hydrogenated egg phosphatidycholine, hydrogenated soya lecithin and distearoyl or dipalmitoyl phosphatidylcholine are preferred such materials. Hydrogenated natural phospholipids or saturated aliphatic phospholipids are believed to work well because the lack of double bonds in the side chains is thought to render the liposomes resistant to oxidation and more physically stable.

The organic solvents may be removed from the solution by rotary evaporation in a round bottom flask leaving a dry film comprised of the complex and other lipid materials. Other equivalent methods of solvent removal are also suitable, such as drying under vacuum. Alternately, the solution can be applied to a spray dryer and solvent removed in a continuous process to produce large quantities of a free flowing yellow powder for liposome preparation. This novel complex thus provides the long awaited continuous production capability sought by industry.

After the last traces of organic solvent have been removed, the dried lipid complex powder may be stored for later use as a starting material for liposome preparation. This product affords the stability necessary for storage previously unavailable to the industry. Thus, the initial chemical steps need not be undertaken each time liposomes are desired.

Liposome preparation is accomplished by first hydrating appropriate quantities of the lipid complex powder with an aqueous buffer, preferably at about 65° C. Aqueous buffer solutions may also contain salts such as sodium chloride, or saccharides such as dextrose or lactose, to achieve any desired osmolarity. The pH of the solution is carefully controlled to achieve a final solution having a pH of about 5.5 or less, generally between about 2.0 and 5.5, preferably between about 4.5 and 5.5.

Liposomes are then formed by the application of shearing force. Typically shearing force can be applied using sonification or homogenization, or by freezing and thawing, dialyzing away a detergent solution from lipids, or other known methods used to prepare liposomes. The size of the liposomes, as well as whether they are multilamellar or unilamellar, can be controlled using a variety of known techniques including the duration of sonication. See Gregoriadis, G. A. Simple Procedure to Preparing Liposomes Capable of High Encapsulation Efficiency Under Mild Conditions. *Liposome Technology*, Gregoriadis, G. A. (ed.) CRC Press: Boca Raton, Florida (1983). The present invention is adaptable, in particular, to scaling up production of the small unilamellar liposomes disclosed in pending Vestar, Inc. application Ser. No. 899,064—Improved Treatment of Systemic Fungal Infections with Phospholipid Particles Encapsulating Polyene Antifungal Antibiotics, incorporated here by reference. Such small liposomes can be sterilized by filtration since their diameter is less than 0.2 $\mu$m. Virtually all of the initial Amphotericin B becomes associated with the liposome fraction when this technique is employed.

These liposome preparations, when formed in saccharide solutions such as 9% lactose, may be lyophilized in vials under suitable conditions to form a dried yellow cake or plug of material. At a later time water may be introduced into the vial to redissolve the solid cake and form a suspension of Amphotericin B liposomes suitable for injection. Lyophilization thus affords the clinician the significant advantage of increased convenience.

Amphotericin B, and other polyene antifungal antibiotics, are amphiphilic. One side of the macrocyclic compound is composed of a series of unsubstituted hydrocarbons with double bonds while the opposing side is substituted with hydroxyl groups. Thus, the molecules tend to exhibit polarity, one side lipophilic and hydrophobic, the other side lipophobic and hydrophilic.

Furthermore, Amphotericin B has one carboxyl group, a Lowry-Brønsted acid, and one amine group, a Lowry-Brønsted base. Therefore, in a neutral pH range of from 5 to 9 the carboxyl group tends to give up a proton while the amine group tends to accept that proton. The net result is that the molecule remains neutral and uncharged while at the same time having two ionized or charged groups—a negatively charged carboxyl group and a positively charged amine group. In that same neutral pH range phospholipid molecules, such as distearoylphosphatidylglycerol are charged. They have an ionized phosphate group giving the molecule a negative charge. Equally, such phospholipid molecules are amphiphilic in that the long alphatic tails are hydrophobic and lipophilic while the ionizable phosphate head is, of course, hydrophilic and lipophobic.

When, however, the phospholipid molecule is solubilized in a protic solvent with a pH between about 1.0 and 3.0, the phospholipid molecule tends to accept a proton and thus form a comparatively neutral molecule. When Amphotericin B is then added to the above acidified solution, the proton of the phosphate group will tend to be transferred to the carboxyl group of the Amphotericin B. The result is that the Amphotericin B molecule will have a net positive charge. Concomitantly, the phospholipid's phosphate group will give up a proton and become negatively charged. The thus formed, oppositely charged, molecules attract; their oppositely charged groups forming an ion pair.

The molecular attraction between Amphotericin B and phosphatidylglycerol is thus greatly increased. The aliphatic hydrocarbon chains of the phospholipids are attracted by hydrophobic interactions to the long chain of unsubstituted double bonds of the polyene. In the specific instance of Amphotericin B, the molecule is a heptaene with seven double bonded carbons along an unsubstituted section of 16 carbon atoms. In the specific instance of distearoylphosphatidylglycerol there are 16 unsubstituted methylene groups between the ester group and terminal methyl group.

In addition to the hydrophobic interaction, the ionized groups form a strong association. In the protonating environment above described, the Amphotericin B will have a positive charge and the phosphatidylglycerol will have a negative charge. Thus, the phosphatidylglycerol and the Amphotericin B will form a strong association.

The strongly associated complex so formed is highly soluble in small amounts of organic solvent. Thus, the disadvantages of the aforementioned prior art methods have been overcome. See, for example, U.S. Pat. No. 4,663,167, May 5, 1987, Lopez-Berestein et al. Accordingly, the present invention provides a procedure for scaling-up production which the industry has long awaited.

A further aspect of the present invention is that the Amphotericin B—phosphatidylglycerol complex will associate with phosphatidylcholine and cholesterol during formulation and will not precipitate out of the organic solvent solution. Furthermore, if the pH of this organic solvent is maintained at 4.5 or less, the complex continues to remain stable and strongly associated. During liposome hydration, the pH of the aqueous buffer is controlled to give a solution having a final pH preferably between about 4.5 and 5.5. At that pH, the Amphotericin B-lipid complex is highly stable and has a high affinity for the lipid bilayer into which it becomes inserted. The result is a decrease in acute toxicity as demonstrated by the following Chart 1:

| Preparation | Liposome Preparation Solution pH | LD50 (mg/kg) |
| --- | --- | --- |
| 1 | 4.6 | 30 |
| 2 | 4.8 | >30* |
| 3 | 5.1 | >30* |

-continued

| Preparation | Liposome Preparation Solution pH | LD50 (mg/kg) |
|---|---|---|
| 4 | 5.6 | 20 |
| 5 | 6.3 | <10 |

Acute Toxicity Test on Mice using Liposomal Formulation Herein Described while Varying Liposomal Preparation Solution pH.
*The decrease in toxicity was so surprisingly great that no upper end point was reached.

Thus, a significant decrease in toxicity is attained using the present invention. The decrease in toxicity allows for an increase in the therapeutic dosages that may be safely administered and thus offers greatly improved methods for Amphotericin B treatment. See U.S. Pat. No. 4,663,167, May 5, 1987, Lopez-Berestein et al.

Furthermore, the associated complex is highly stable during storage. The liposomes formed from either a film, or spray dried powder, after hydration with a saccharide buffer, may be lyophilized. The lyophilized cake can be stored preferably in a sterile lyophilization vial and later rehydrated with sterile water for injection. The reconstituted liposomes retain therapeutic efficacy.

EXAMPLE 1

Formation of Amphotericin B—Phosphatidylglycerol Complex 632.7 mg distearoylphosphatidylglycerol sodium salt (Avanti Polar Lipids, Birmingham, Ala.) was dissolved in 4 ml of an equivolume solution of chloroform and methanol at 65° Centigrade. 300 ul 2.5 M HCl was added to the solution. 375.9 mg Amphotericin B (Squibb Pharmaceuticals, New Brunswick, N.J.) was first suspended in 4.0 ml of equivolume solution of chloroform and methanol, and then the suspension was added to the acidified DSPG solution. The Amphotericin B—DSPG lipophilic complex was formed with heating at 65° C. for several minutes yielding an orange solution of the dissolved Amphotericin B complex with a pH of approximately 1.5. The concentration of Amphotericin B was approximately 45 mg/ml.

1598.4 mg hydrogenated egg phosphatidylcholine (Avanti Polar Lipids) was dissolved in 4.5 ml of an equivolume solution of chloroform and methanol at 65° C. to yield a clear solution. 393 mg cholesterol (Sigma Chemical Co.) was also dissolved in a 4.5 ml equivolume solution of chloroform and methanol at 65° C. to yield a clear solution. The cholesterol and hydrogenated egg phosphatidylcholine solutions were then mixed with the Amphotericin B—DSPG complex solution giving a translucent orange solution. 175 ul NaOH 2.5 M was then added to this solution to yield a pH of approximately 4.5. The weight of total dissolved solids was between 15 and 20% on a weight to volume basis.

The formulation in this example has the following molar ratio:

| | |
|---|---|
| Amphotericin B | 0.4 |
| Distearoylphosphatidylglycerol | 0.8 |
| Hydrogenated Egg Phosphatidylcholine | 2.0 |
| Cholesterol | 1.0 |

Other formulations are listed in Table 1.

Those formulations demonstrate that the invention is equally suitable to other formulations. The molar ratio of the primary component lipid to sterol may vary from at least 1:1 to 4:1. Similarly, the molar ratio of polyene to charged phospholipid may vary at least from 0.5:1 to 4:1.

Formation of Spray Dried Powder

The lipid solution containing the novel Amphotericin B—DSPG complex contains only small amounts of organic solvent and consequently can be spray dried to a powder in a manner making the invention uniquely suitable to continuous flow manufacturing procedures. The invention thus allows for scaled-up production of liposomes as compared to the prior art. The spray dried powder thus formed can be stored.

In one preferred embodiment, the lipid solution containing the Amphotericin B—DSPG complex was pumped as a fine mist into the spray dryer apparatus with an inlet temperature of 45° C. A free flowing yellow to light orange powder resulted. The powder so formed was collected and stored at −20° C. in a desiccator.

Amphotericin B Liposome Preparation

The stored powder can then be hydrated in any quantity and used at any time to form liposomes for treatment of fungal infection. In one preferred embodiment, it is desirable to simultaneously sterilize the finished liposome preparation. Thus, small unilamellar vesicles were desired which could be sterilized by filtration through a 0.22 μm pore size filter.

15 gm of the spray dried powder was hydrated in 750 ml aqueous buffer of 9% (w/v) lactose containing 10 millimolar sodium succinate at pH 5.5 warmed to 65° C. for 40 to 60 minutes. The shearing force to form the small unilamellar vesicles was provided by a 10 minute exposure to a high shear force emulsification technique (see pending Vestar, Inc. application Ser. No. 696,727; now U.S. Pat. No. 4,753, 788).

Characterization of Liposomes

The concentration of components of the above described preferred embodiment were determined by high performance liquid chromatography and are shown below. The mean liposome diameter was determined to be 38.3 nm by dynamic light scattering.

| Component | Concentration |
|---|---|
| Amphotericin B | 1.86 mg/ml |
| Hydrogenated Egg PC | 10.12 mg/ml |
| Cholesterol | 2.21 mg/ml |
| Distearoyl Phosphatidyl glycerol | 4.29 mg/ml |

EXAMPLE 2

Additional Formulation Compositions of AMB Liposomes

Several studies were performed in order to evaluate the effect of altering the ratios of various components in the liposome formulation. These studies provide evidence for the unique advantage the Amphotericin B phosphatidylglycerol complex provides in liposome preparation. Thus, preparation 1 in Table 1, in which phosphatidylglycerol was omitted, did not form AmB liposome. However, when distearoyl phosphatidylglycerol was added in the molar ratio of 0.5 to 2.5 times that of Amphotericin B (preparations 2–6, Table 1) liposomes were formed.

The importance of the added cholesterol is illustrated in preparations 7–10, Table 1. Although liposomes could be formed with the Amphotericin B-phosphatidylglycerol complex in the absence of cholesterol (preparation 7) or with a low concentration of cholesterol (preparation 8), these preparations were more toxic than preparations 9 or 10 in which cholesterol content was increased. Thus, the molar ratio of cholesterol to phosphatidylcholine was optimal in the range of 1:4 to 1:1.

Alternatives to hydrogenated egg phosphatidylcholine were investigated and results are summarized in Table 1, preparations 11 and 12. Hydrogenated soybean phosphatidylcholine and distearoyl phosphatidylcholine formed satisfactory Amphotericin B liposomes.

Preparation 13 in Table 1 demonstrates that distearoyl phosphatidylglycerol can be replaced by dilauroyl phosphatidylglycerol. The lipid soluble complex with Amphotericin B was formed and satisfactorily incorporated into liposomes.

EXAMPLE 3

Antifungal Efficacy of Amphotericin B Liposomes 360.1 mg of the spray dried powder were hydrated at 65 degrees Centigrade for 40 minutes with 9% lactose containing 10 mM succinate buffer, pH 5.62. Liposomes were prepared by sonication for four minutes with a ½ probe at 65° C. under a nitrogen atmosphere. Three successive batches of liposomes were prepared in a similar fashion. After sterile filtration, the Amphotericin B concentration was determined to be 1.73 mg/ml.

For therapeutic efficacy studies, groups of 8 mice were given intravenous inoculations of $3.5 \times 10^5$ Candida albicans yeast cells. Three days post-infection, animals were treated with a single dose of either free Amphotericin B or liposomal Amphotericin B. A severe systemic infection existed in animals which were not treated until three days post infection. Each successive group was treated with an increasing dose of medicament in order to establish a dose response relationship. Twenty-nine days after infection the study was evaluated for surviving animals. All untreated control animals had died by 8 days post-infection, with a median survival of 7 days. There was no dose level of free Amphotericin B which produced any survivors at 29 days post infection. In contrast, all animals treated with 10 or 15 mg/kg of liposomal Amphotericin B were still alive 42 days post infection. The complete response to the free and liposomal Amphotericin B is shown in Table 2.

EXAMPLE 4

Stability of Liposome Amphotericin B To Lyophilization

The presence of lactose or other saccharides as excipients in the liposome Amphotericin B formulation serves to stabilize the integrity of the physical structure of the liposome during lyophilization. Thus, the formulations herein described can be lyophilized under appropriate conditions, and the lyophilized cake or plug can be reconstituted with sterile water at a later date.

The effect of lyophilization of four separate preparation's of liposome Amphotericin B has been evaluated. In all cases the preparation contained 9% lactose as an excipient. In some cases, lyophilization and rehydration caused the mean liposome diameter to increase from about 40 nm to about 70 nm. Acute toxicity increased from >30 mg/kg to 20–25 mg/kg Amphotericitn B when the rehydration was carried out at 22° C. However, if the same preparation was rehydrated at 65° C., there was no apparent increase in toxicity (see experiment 3, Table 3).

Additional results are summarized in Table 3.

The foregoing description of the invention and the examples demonstrating the application of the invention to production of Amphotericin B—lipid liposomes of illustrated size, structure and medical utility are but exemplary of the various ways the invention can be utilized. That other variations will be useful will be apparent to those skilled in the art. Therefore, the present invention is to be considered limited only by the appended claims.

TABLE 1

PROPERTIES OF VARIOUS FORMULATIONS OF LIPOSOME AMPHOTERICIN B

| PREPARATION | COMPONENTS | MOLAR RATIO OF COMPONENTS | % AMB INCORP. | LIPOSOME DIAMETER (NM) | ACTUE TOXICITY (LD50) |
|---|---|---|---|---|---|
| 1. | Hydr. Egg PC:Chol:DSPG:AMB | 2:1:0:0.4 | [DOES NOT FORM AMB LIPOSOMES] | | |
| 2. | Hydr. Egg PC:Chol:DSPG:AMB | 2:1:0.2:0.4 | 75 | 41 | ND |
| 3. | Hydr. Egg PC:Chol:DSPG:AMB | 2:1:0.4:0.4 | 91 | 41 | ND |
| 4. | Hydr. Egg PC:Chol:DSPG:AMB | 2:1:0.4:0.4 | 94 | 36 | ND |
| 5. | Hydr. Egg PC:Chol:DSPG:AMB | 2:1:0.8:0.4 | 100 | 39.3 | ND |
| 6. | Hydr. Egg PC:Chol:DSPG:AMB | 2:1:1:0.4 | 82 | 30.8 | ND |
| 7. | Hydr. Egg PC:Chol:DSPG:AMB | 2:1:0.8:0.4 | 82 | 53.6 | <20 MG/KG |
| 8. | Hydr. Egg PC:Chol:DSPG:AMB | 2:0.5:0.8:0.4 | 68 | 53.7 | <20 MG/KG |
| 9. | Hydr. Egg PC:Chol:DSPG:AMB | 2:1:0.8:0.4 | 85 | 40.3 | >30 MG/KG |
| 10. | Hydr. Egg PC:Chol:DSPG:AMB | 2:1.5:0.8:0.4 | 64 | 46.8 | 20 MG/KG |
| 11. | DSPC:Chol:DSPG:AMB | 2:1:0.8:0.4 | 68 | 44.5 | >30 MG/KG |
| 12. | Hydr. Soya PC:Chol:DSPG:AMB | 2:1:0.8:0.4 | 100 | 42.9 | >30 MG/KG |
| 13. | Hydr. Egg. PC:Chol:DLPG:AMB | 2:1:0.8:0.4 | 84 | 41.4 | ND |

ND = Not Determined

TABLE 2

THERAPEUTIC EFFICIENCY OF LIPOSOMAL AMPHOTERICIN B IN *C. albicans* INFECTED MICE

| TREATMENT | AMB DOSE mg/kg | 29 SURVIVORS[1] | 3 DAY POST INFECTION THERAPY |
|---|---|---|---|
| CONTROL[2] | — | | 0 |
| FREE AM B | 0.5 | 0 | (0%) |
| | 1.0 | 0 | (0%) |
| | 1.5 | 0 | (0%) |
| LIPOSOME AM B | 1.0 | 0 | (0%) |
| | 2.5 | 3 | (38%) |
| | 5.0 | 4 | (50%) |
| | 7.5 | 6 | (75%) |
| | 10.0 | 8 | (100%) |
| | 15.0 | 8 | (100%) |
| | 20.0 | 4 | (50%) |

[1] n = 8 Animals per group.
[2] Control median life span was 7 days.

TABLE 3

Effect of Lyophilization on Liposome Amphotericin B

| Experiment | Conditions | Liposome Diameter (nm) | Ampho B Conc. (mg/ml) | Acute Toxicity (LD50 mice) | Rehydration Temperature (degree C) |
|---|---|---|---|---|---|
| 1. | Before Lyo. | 38.3 | 1.86 | >30 mg/kg | |
| | After Lyo. | 69.9 | 1.60 | >30 mg/kg | 65 |
| 2. | Before Lyo. | 45.3 | 1.75 | >30 mg/kg | |
| | After Lyo. | 45.1 | 1.56 | >30 mg/kg | 65 |
| 3. | Before Lyo. | 42.4 | 1.72 | >30 mg/kg | |
| | After Lyo. | 66.9 | 1.72 | 25 mg/kg | 22 |
| | After Lyo. | 61.8 | 1.69 | >30 mg/kg | 65 |
| 4. | Before Lyo. | 40.3 | 1.88 | >30 mg/kg | |
| | After Lyo. | 70.6 | 1.90 | 20 mg/kg | 22 |

We claim:

1. A process for forming a soluble complex of an amphiphilic drug selected from the group consisting of polyene antibiotics, comprising forming a soluble complex of the amphiphilic drug and a phosphatidylglycerol in an acidified organic solvent having a pH of 1.0–3.0.

2. The process of claim 1 in which the phosphatidylglycerol is selected from the group consisting of distearoylphosphatidylglycerol, dilaurylphosphatidylglycerol, and dimyristoylphosphatidylglycerol.

3. The process of claim 1 in which the amphiphilic drug is amphotericin B.

4. The process of claim 2 in which the amphiphilic drug is amphotericin B.

5. The process of claim 3 in which the phosphatidylglycerol is distearoylphosphatidylglycerol.

6. A process for the formation of liposomes containing a polyene antibiotic, comprising forming a complex of a polyene antibiotic and a phosphatidylglylcerol in an acidified organic solvent having a pH of 1.0–3.0, removing the organic solvent to form a dried complex, and hydrating the dried complex with an aqueous medium to form liposomes having a diameter of less than 0.2 µm.

7. The process of claim 6 in which the phosphatidylglycerol is selected from the group consisting of distearoylphosphatidylglycerol, dilaurylphosphatidylcglycerol, and dimyristoylphosphatidylglycerol.

8. The process of claim 6 in which a sterol is included with the complex during hydration to form liposomes containing a polyene antibiotic and a sterol.

9. The process of claim 7 in which a sterol is included with the complex during hydration to form liposomes containing a polyene antibiotic and a sterol.

* * * * *